United States Patent
Ken et al.

[11] Patent Number: 6,013,084
[45] Date of Patent: *Jan. 11, 2000

[54] STRETCH RESISTANT VASO-OCCLUSIVE COILS (II)

[75] Inventors: Christopher G. M. Ken, San Mateo; Joseph C. Eder, Los Altos Hills; Clifford Teoh, Daly City, all of Calif.

[73] Assignee: Target Therapeutics, Inc., Fremont, Calif.

[*] Notice: This patent is subject to a terminal disclaimer.

[21] Appl. No.: 08/879,408

[22] Filed: Jun. 20, 1997

Related U.S. Application Data

[63] Continuation-in-part of application No. 08/607,593, Feb. 27, 1996, abandoned, and application No. 08/717,285, Sep. 20, 1996, Pat. No. 5,833,705, which is a continuation-in-part of application No. 08/497,331, Jun. 30, 1995, Pat. No. 5,582,619.

[51] Int. Cl.$^7$ .................................................. A61M 29/00
[52] U.S. Cl. ............................................ 606/108; 606/191
[58] Field of Search ............................ 606/198, 192, 606/191, 108, 1; 623/12

[56] References Cited

U.S. PATENT DOCUMENTS

| | | |
|---|---|---|
| 3,174,851 | 3/1965 | Buehler et al. . |
| 3,351,463 | 11/1967 | Rozner et al. . |
| 3,753,700 | 8/1973 | Harrison et al. . |
| 4,994,069 | 2/1991 | Ritchart et al. . |
| 5,122,136 | 6/1992 | Guglielmi et al. . |
| 5,217,484 | 6/1993 | Marks . |

(List continued on next page.)

FOREIGN PATENT DOCUMENTS

| | | |
|---|---|---|
| 0754435 | 1/1997 | European Pat. Off. . |
| 0 792 623 A1 | 9/1997 | European Pat. Off. . |

*Primary Examiner*—Michael Buiz
*Assistant Examiner*—Kevin Truong
*Attorney, Agent, or Firm*—Morrison & Foerster, LLP

[57] ABSTRACT

This is an implantable vaso-occlusive device. It is typically a vaso-occlusive coil comprising a primary helically wound coil which may then be wound into a secondary shape. Central to the invention is the use of a stretch-resisting member extending through the lumen formed, which stretch-resisting member is fixedly attached, directly or indirectly, to the coil in at least two locations. The stretch-resisting member is preferably somewhat loose within the interior of the lumen so to prevent the coil from collapsing, binding, and therefore stiffening during passage of turns through the human body. The coil should bend easily. In some variations of the invention, the stretch-resisting member may be formed into coil tips at the ends of the coil using simple equipment such as soldering irons or the like. The tips are typically of the same diameter as is the coil body itself. This stretch-resisting member is for the primary purpose of preventing stretching of the coil during movement of that coil, e.g., by retrieval or repositioning after deployment. The device may have a self-forming secondary shape made from a pre-formed primary linear helically wound coil, although it need not have the secondary form. Desirably, the coil is extremely flexible and is controllaby released using a severable or mechanical joint such as an electrolytically detachable joint. External fibers may be attached to the device and affixed to the pre-formed linear member to increase thrombogenicity. The extremely flexible variation of the invention may be hydraulically delivered through the lumen of a catheter and is so flexible that it may be retrievably delivered therethrough a flow-directed catheter. The vaso-occlusive member may be also be covered with a fibrous braid. The device is typically introduced into the body through a catheter. The device is passed axially through the catheter sheath and assumes its secondary form upon exiting the catheter.

44 Claims, 10 Drawing Sheets

U.S. PATENT DOCUMENTS

| | | |
|---|---|---|
| 5,226,911 | 7/1993 | Chee et al. . |
| 5,234,437 | 8/1993 | Sepetka . |
| 5,250,071 | 10/1993 | Palermo . |
| 5,261,916 | 11/1993 | Engelson . |
| 5,304,194 | 4/1994 | Chee et al. . |
| 5,304,195 | 4/1994 | Twyford, Jr. et al. . |
| 5,312,415 | 5/1994 | Palermo . |
| 5,336,205 | 8/1994 | Zenzen et al. . |
| 5,350,397 | 9/1994 | Palermo et al. . |
| 5,354,295 | 10/1994 | Guglielmi et al. . |
| 5,382,259 | 1/1995 | Phelps et al. . |
| 5,387,219 | 2/1995 | Rappe . |
| 5,582,619 | 12/1996 | Ken ........................................ 606/191 |
| 5,601,600 | 2/1997 | Ton ........................................ 606/198 |
| 5,645,558 | 7/1997 | Horton . |
| 5,658,308 | 8/1997 | Snyder ................................... 606/198 |

STRETCH RESISTANT VASO-OCCLUSIVE COILS (II)

RELATED APPLICATIONS

This is a continuation-in-part of U.S. Ser. No. 08/607,593, filed Feb. 27, 1996, now abandoned and Ser. No. 08/717,285, filed Sep. 20, 1996 (now U.S. Pat. No. 5,833,705), which is a continuation-in-part of Ser. No. 08/497,331, filed Jun. 30, 1995 (issued as U.S. Pat. No. 5,582,619 on Dec. 10, 1996), the entirety of which are incorporated by reference.

FIELD OF THE INVENTION

This invention is an implantable vaso-occlusive device. It is typically a vaso-occlusive coil comprising a primary helically wound coil which may then be wound into a secondary shape. Central to the invention is the use of a stretch-resisting member extending through the lumen formed, which stretch-resisting member is fixedly attached, directly or indirectly, to the coil in at least two locations. The stretch-resisting member in this variation desirably is heat-treated in situ when the coil is in the secondary shape. This heat treatment allows the stretch-resisting member to conform to the shape of the coil in its secondary configuration. Desirably, the member does not appreciably affect the inherent secondary shape of the coil. The stretch-resisting member is preferably somewhat loose within the interior of the lumen so to prevent the coil from collapsing, binding, and therefore stiffening during passage of turns through the human body. The coil should bend easily. In some variations of the invention, the stretch-resisting member may be formed into coil tips at the ends of the coil using simple equipment such as soldering irons or the like. The tips are typically of the same diameter as is the coil body itself. This stretch-resisting member is for the primary purpose of preventing stretching of the coil during movement of that coil, e.g., by retrieval or repositioning after deployment. The device may have a self-forming secondary shape made from a pre-formed primary linear helically wound coil, although it need not have the secondary form. Desirably, the coil is extremely flexible and is controllaby released using a severable or mechanical joint such as an electrolytically detachable joint. External fibers may be attached to the device and affixed to the pre-formed linear member to increase thrombogenicity. The extremely flexible variation of the invention may be hydraulically delivered through the lumen of a catheter and is so flexible that it may be retrievably delivered therethrough a flow-directed catheter. The vaso-occlusive member may be also be covered with a fibrous braid. The device is typically introduced into the body through a catheter. The device is passed axially through the catheter sheath and assumes its secondary form upon exiting the catheter.

BACKGROUND OF THE INVENTION

Vaso-occlusion devices are surgical implements or implants that are placed within the vasculature of the human body, typically via a catheter, either to block the flow of blood through a vessel making up that portion of the vasculature via the formation of an embolus or to form such an embolus within an aneurysm stemming from the vessel. One widely used vaso-occlusive device is a helical wire coil having windings which may be dimensioned to engage the walls of the vessels. Other less stiff, helically coiled devices have been described, as well as those involving woven braids. Virtually all such vaso-occlusive implants are delivered by wire-guided catheters which devices are pushed through the catheter. Because of the need for a pusher and concerns for recovery of such vaso-occlusive devices should they be malplaced in the body, it is unlikely that prior to this invention has there been a vaso-occlusive device of a form similar to this delivered through a flow directed catheter.

As an instance of an early vaso-occlusive device, U.S. Pat. No. 4,994,069, to Ritchart et al., describes a vaso-occlusive coil that assumes a linear helical configuration when stretched and a folded, convoluted configuration when relaxed. The stretched condition is used in placing the coil at the desired site (by its passage through the catheter) and the coil assumes a relaxed configuration—which is better suited to occlude the vessel—once the device is so placed. Ritchart et al. describes a variety of shapes. The secondary shapes of the disclosed coils include "flower" shapes and double vortices. A random secondary shape is described, as well.

Vaso-occlusive coils having attached fibrous elements in a variety of secondary shapes are shown in U.S. Pat. No. 5,304,194, to Chee et al. Chee et al. describes a helically wound device having a secondary shape in which the fibrous elements extend in a sinusoidal fashion down the length of the coil. These coils, as with Ritchart et al., are produced in such a way that they will pass through the lumen of a catheter in a generally straight configuration and, when released from the catheter, form a relaxed or folded shape in the lumen or cavity chosen within the human body. The fibrous elements shown in Chee et al. enhance the ability of the coil to fill space within the vasculature and to facilitate formation of embolus and subsequent allied tissue.

There are a variety of ways of discharging shaped coils and linear coils into the human vasculature. In addition to those patents which apparently describe only the physical pushing of a coil out into the vasculature (e.g., Ritchart et al.), there are a number of other ways to release the coil at a specifically chosen time and site. U.S. Pat. No. 5,354,295 and its parent, U.S. Pat. No. 5,122,136, both to Guglielmi et al., describe an electrolytically detachable embolic device.

A variety of mechanically detachable devices are also known. For instance, U.S. Pat. No. 5,234,437, to Sepetka, shows a method of unscrewing a helically wound coil from a pusher having interlocking surfaces. U.S. Pat. No. 5,250,071, to Palermo, shows an embolic coil assembly using interlocking clasps mounted both on the pusher and on the embolic coil. U.S. Pat. No. 5,261,916, to Engelson, shows a detachable pusher-vaso-occlusive coil assembly having an interlocking ball and keyway-type coupling. U.S. Pat. No. 5,304,195, to Twyford et al., shows a pusher-vaso-occlusive coil assembly having an affixed, proximally extending wire carrying a ball on its proximal end and a pusher having a similar end. The two ends are interlocked and disengage when expelled from the distal tip of the catheter. U.S. Pat. No. 5,312,415, to Palermo, also shows a method for discharging numerous coils from a single pusher by use of a guidewire which has a section capable of interconnecting with the interior of the helically wound coil. U.S. Pat. No. 5,350,397, to Palermo et al., shows a pusher having a throat at its distal end and a pusher through its axis. The pusher sheath will hold onto the end of an embolic coil and will then be released upon pushing the axially placed pusher wire against the member found on the proximal end of the vaso-occlusive coil. coil.

Vaso-occlusive coils having little or no inherent secondary shape have also been described. For instance, in U.S. patent application Ser. No. 07/978,320, filed Nov. 18, 1992, entitled "Ultrasoft Embolization Coils with Fluid-Like Properties" by Berenstein et al., is found a coil having little or no shape after introduction into the vascular space.

None of these devices are helical coils which contain a stretch-resisting member contained therein.

SUMMARY OF THE INVENTION

This invention is a vaso-occlusive device comprising a helically wound coil which is formed by winding a wire into a first or primary helix to form an outer helical member having first and second ends. A stretch resistant member extending through the lumen thus-formed is fixedly attached, directly or indirectly, to the coil in at least two locations. The stretch-resisting member is preferably loose within the coil to prevent binding of the coil during passage of the coil through turns in the vasculature.

The primary helix or "primary form" may be wound into a secondary form and heat-treated to preserve that form, desirably prior to the step of including the stretch-resisting member into the coil. The coil, with its included stretch-resisting member, will be again heat-treated to shape that the stretch-resisting member into the coil's secondary form. The secondary form may be one which, when ejected from a delivery catheter, forms a specific shape. Such a shape might, e.g., fill a vascular cavity such as an aneurysm, or perhaps, a fistula or AVM. The stiffness of the various parts of the coil may be tailored to enhance the utility of the device for specific applications. Extremely flexible coils are highly desirable. Fibrous materials may be woven into the member or tied or wrapped onto it to enhance the thrombogenicity.

Once the secondary form of the coil has been achieved, the stretchresisting member is then inserted into the lumen, and secured to the coil. The assembly is then gently heat-treated to allow the stretch-resisting member to assume the secondary form of the coil.

The device is used simply by temporarily straightening the device, as necessary, and introducing it into a suitable catheter, the catheter already having been situated so that its distal opening is at the selected site in the body. The device is then pushed through the catheter and, upon its ejection from the distal end of the catheter into the vascular cavity, assumes its relaxed or secondary shape.

The device is typically used in the human vasculature to form emboli but may be used at any site in the human body where an occlusion such as one produced by the inventive device is needed.

Also forming an important aspect of this invention is the combination of this inventive vaso-occlusive device with a flow-directed catheter.

BRIEF DESCRIPTION OF TILE DRAWINGS

Figure 2A:
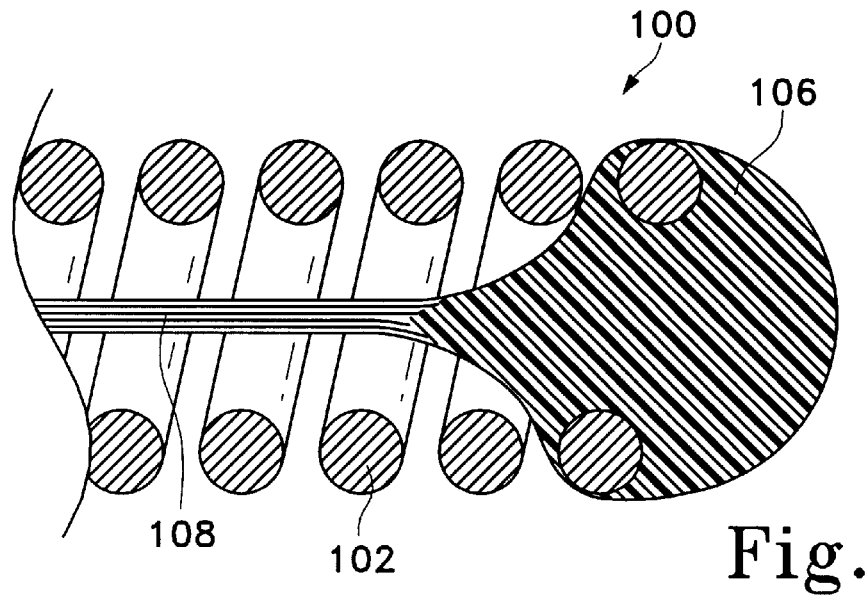
Figure 2B:
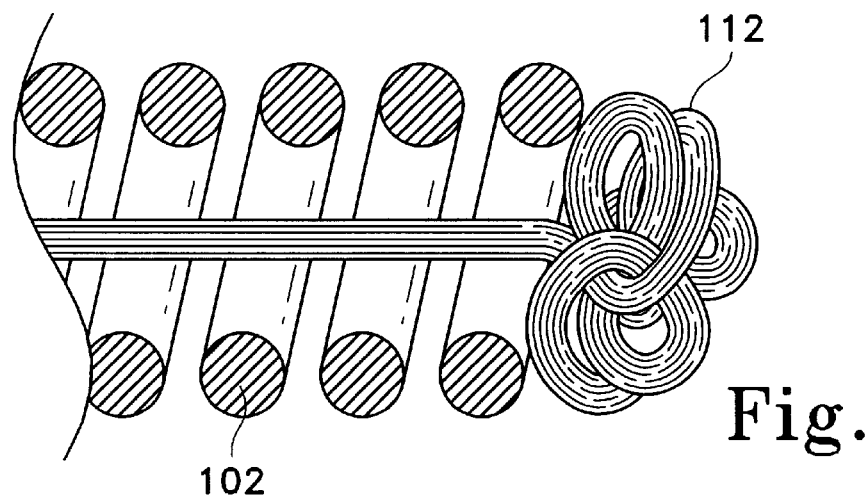
Figure 2C:
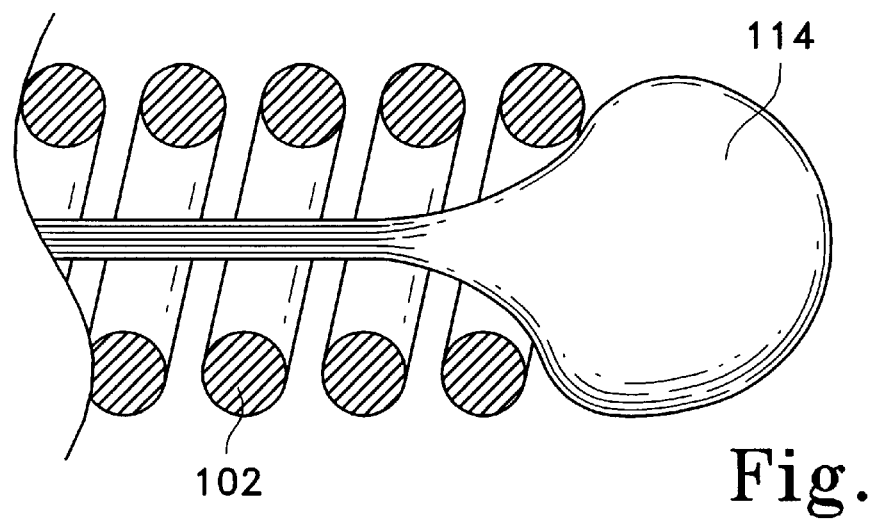

FIGS. 2A, 2B, and 2C show side view, partial cutaways of typical ends of the inventive vaso-occlusive coils.

Figure 3A:
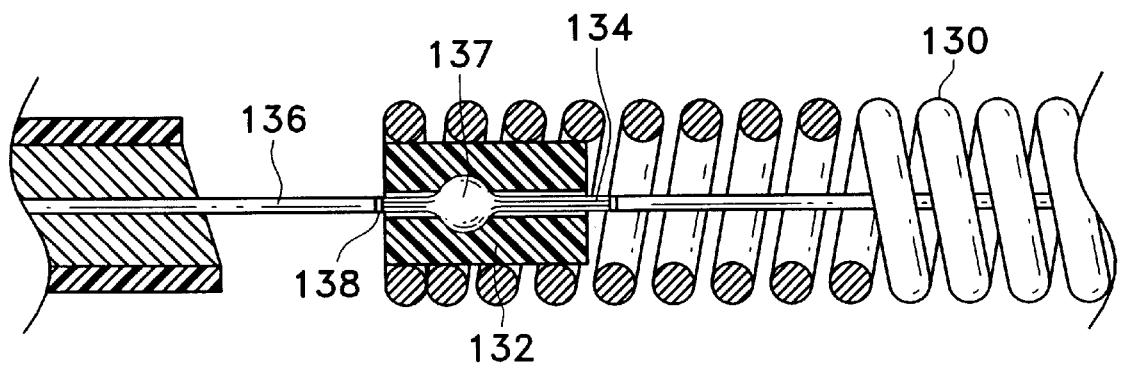
Figure 3B:
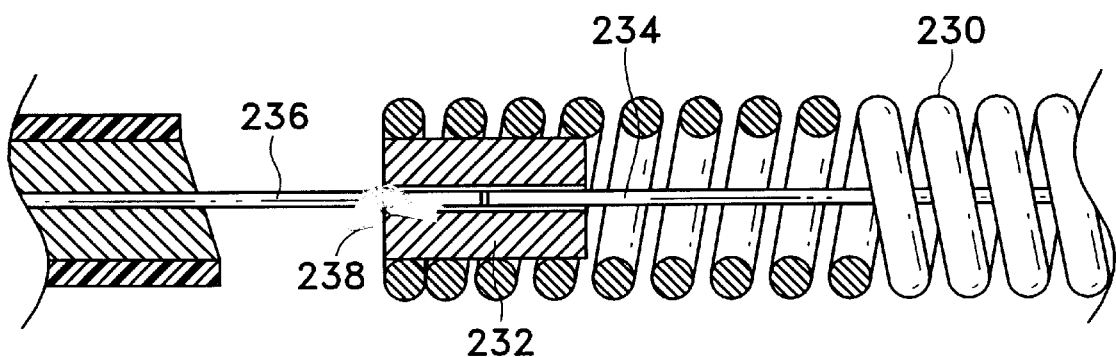
Figure 3C:
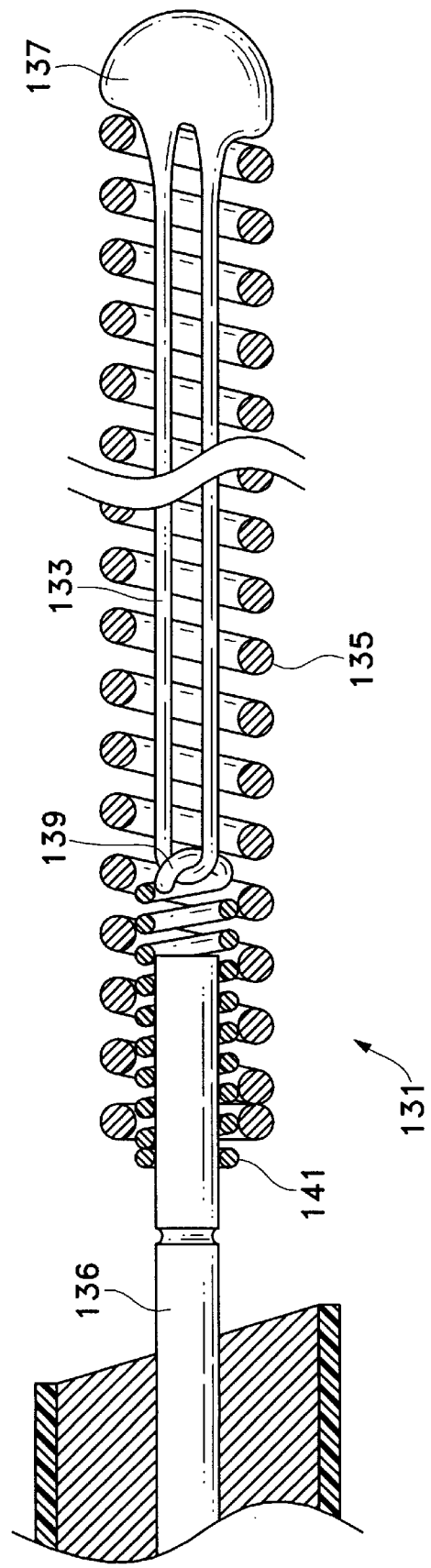

FIGS. 3A, 3B, and 3C show side view cutaways of electrolytically severable joints in combination with a vaso-occlusive coil made according to the invention.

Figure 4A:
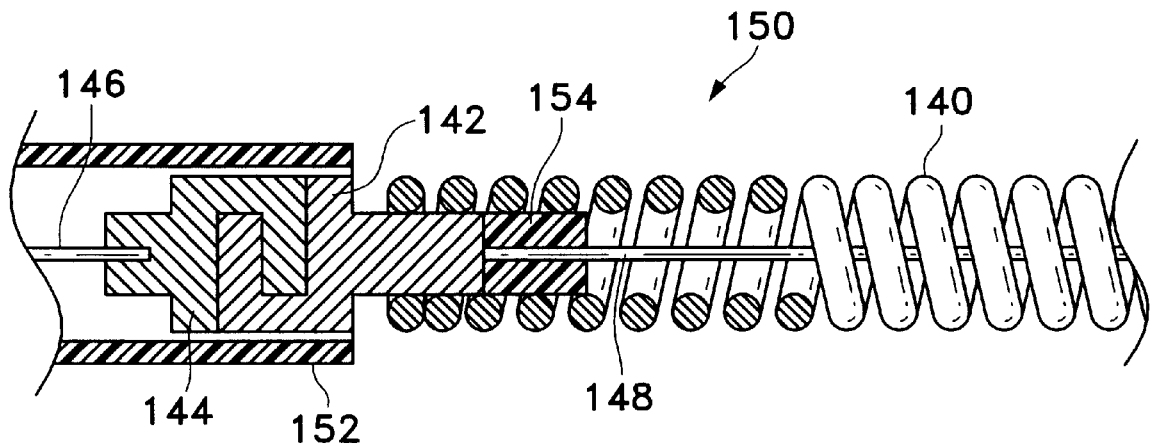
Figure 4B:
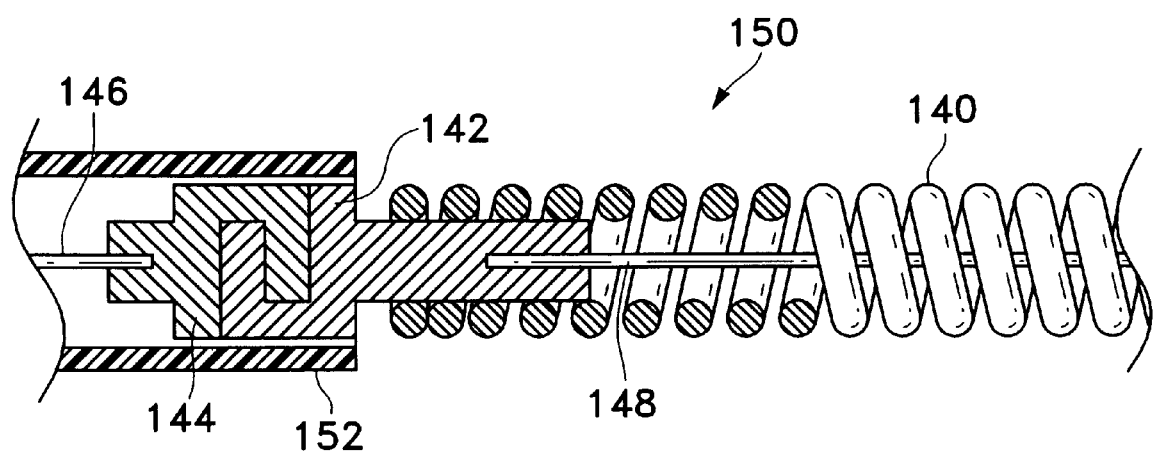

FIGS. 4A and 4B show a side view, partial cutaway of a typical mechanically detachable joint in combination with a vaso-occlusive coil made according to the invention.

Figure 5:
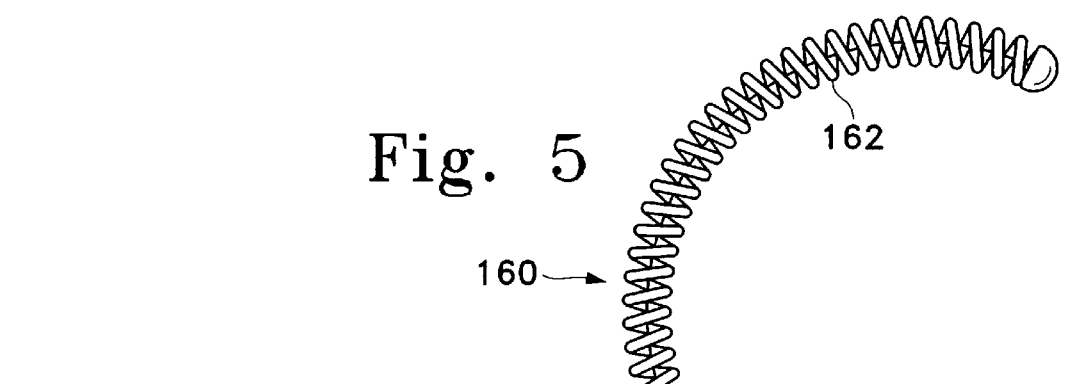

FIG. 5 shows a "C" shaped secondary configuration for the inventive vaso-occlusive device.

Figure 6:
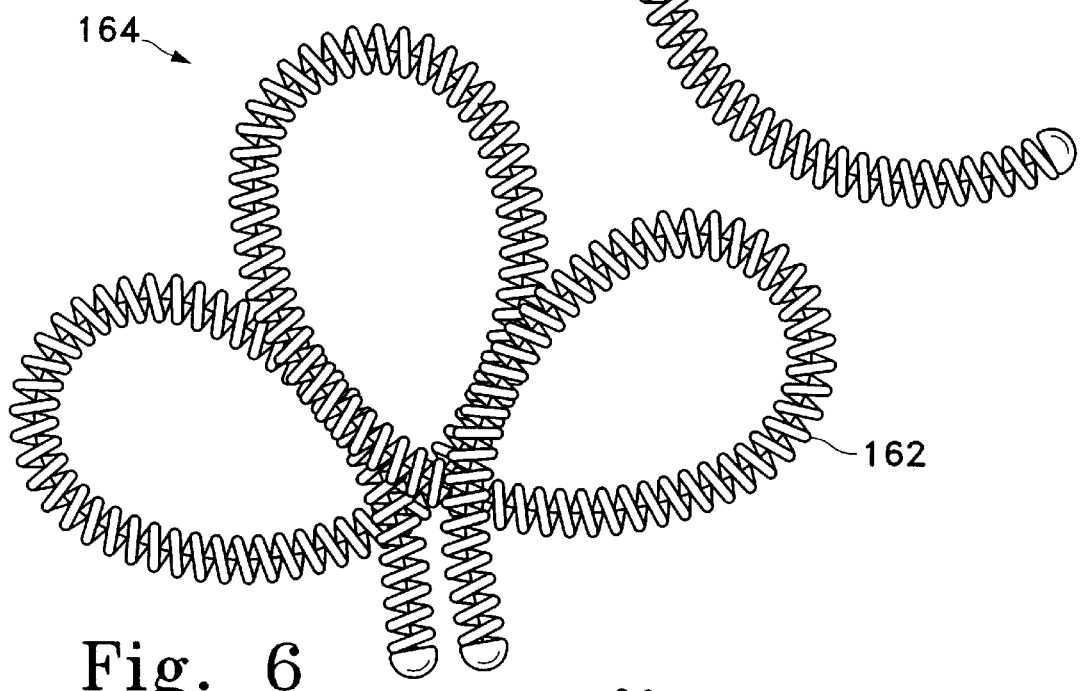

FIG. 6 shows a clover-leaf secondary shape for the inventive vaso-occlusive device.

Figure 7:
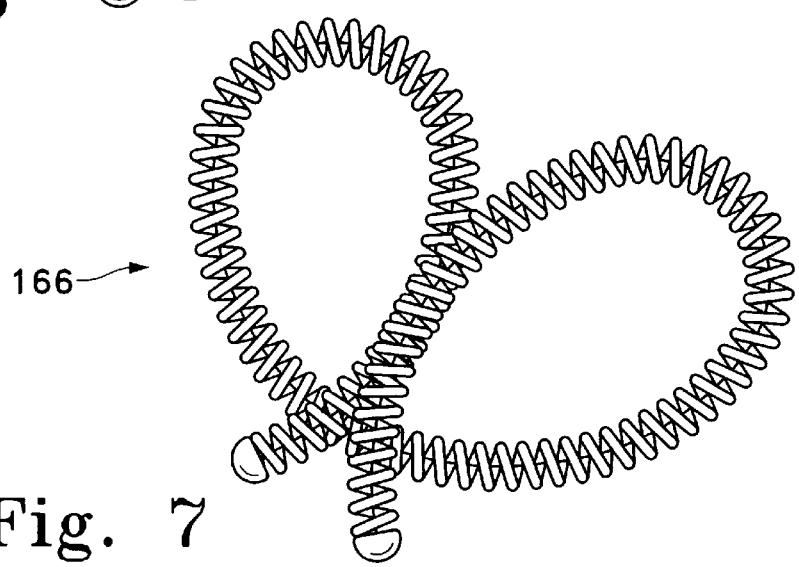

FIG. 7 shows a double-looped secondary shape for the inventive vaso-occlusive device.

Figure 8:
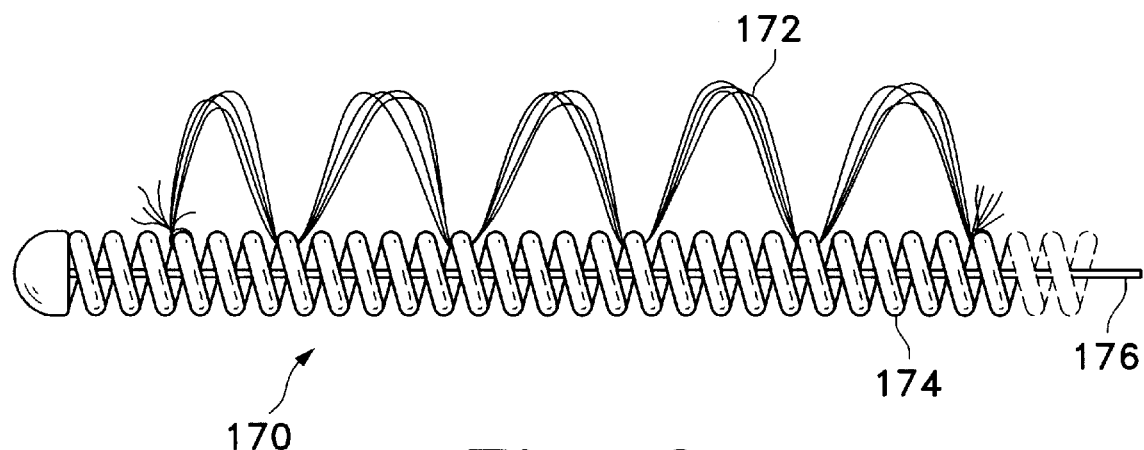

FIG. 8 shows attachment of external fibrous material to the inventive vaso-occlusive device.

Figure 9:
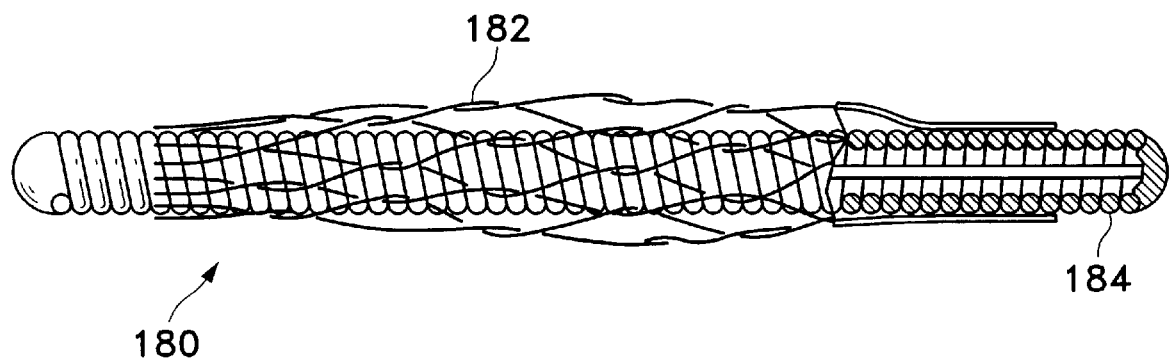

FIG. 9 shows attachment of external braided fibrous material to the inventive vaso-occlusive device.

Figure 10:
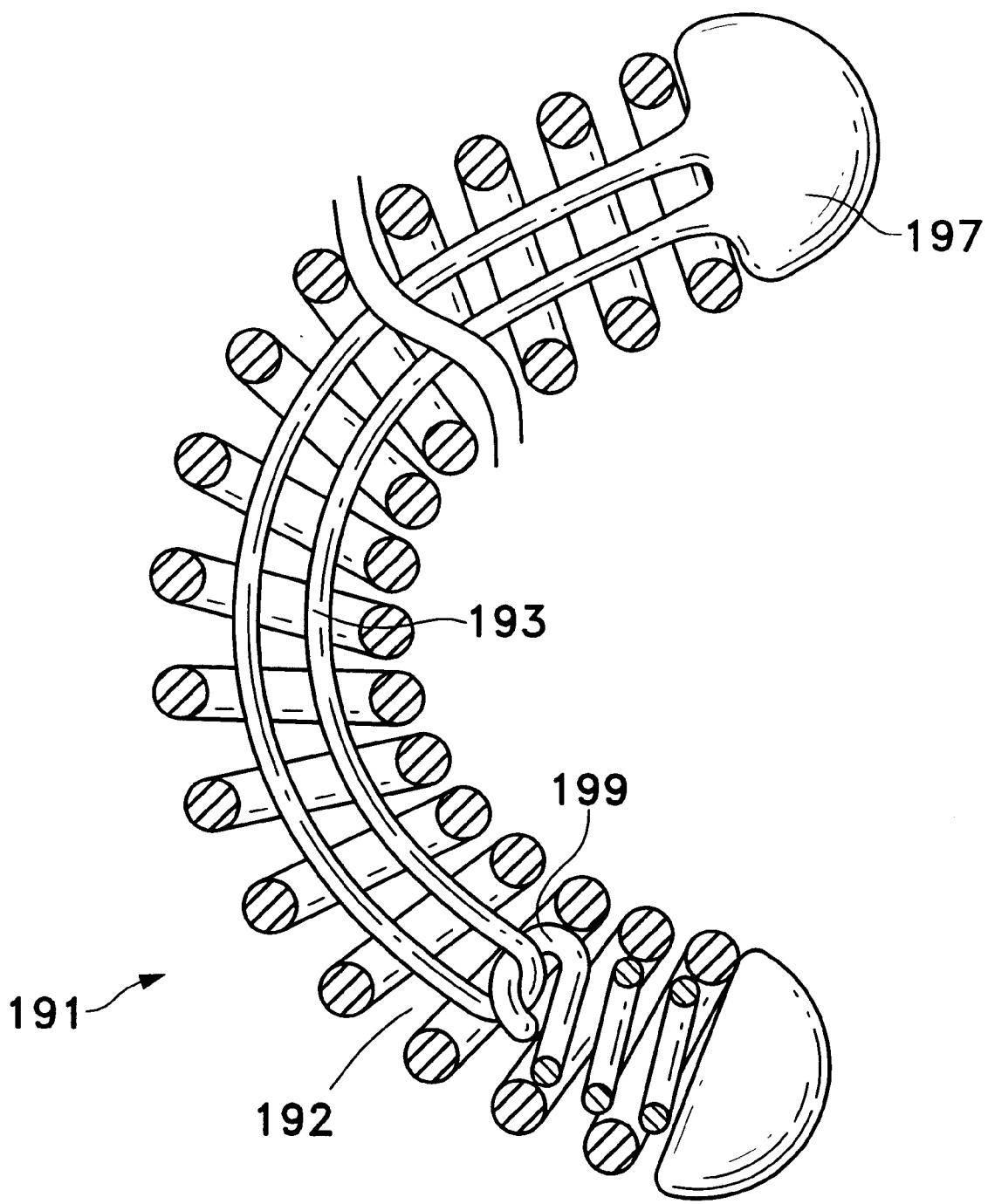

FIG. 10 shows the vaso-occlusive device of the invention in which a polymer is introduced into the lumen of a coil after it has been shaped to return to its secondary form.

Figure 11:
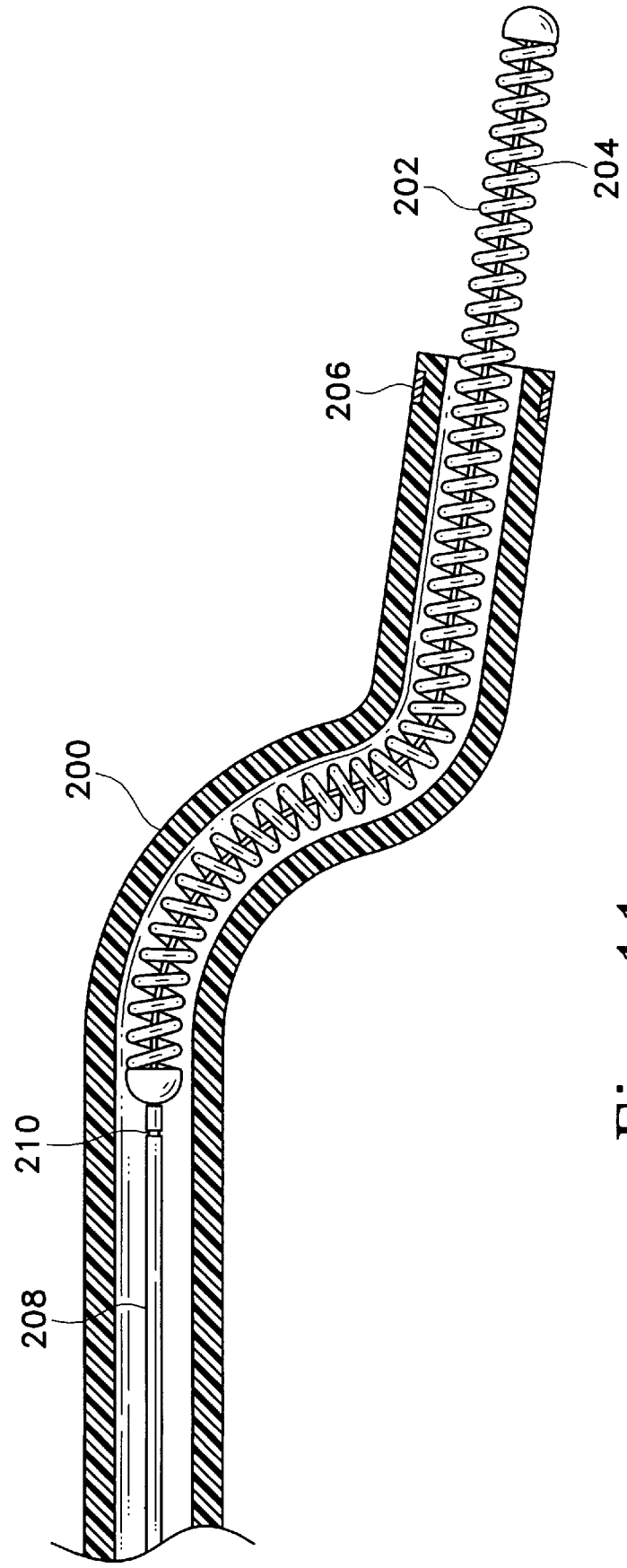

FIG. 11 shows the combination of the vaso-occlusive device of this invention in assembly with a flow-directed catheter.

FIGS. 12A–12D show a procedure for introducing a vaso-occlusive coil such as found in the other FIGS. into an aneurysm.

DESCRIPTION OF THE INVENTION

Figure 1A:
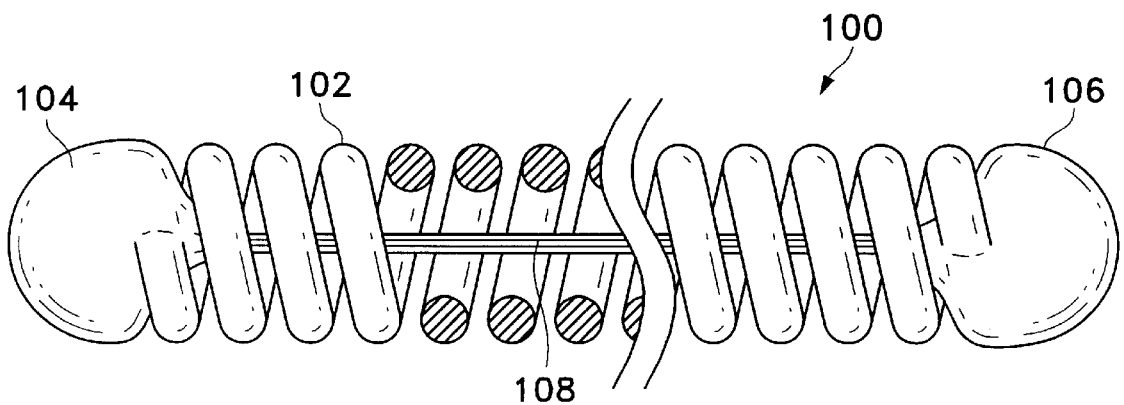
FIG. 1A shows a side view, partial cutaway of a vaso-occlusive coil made according to the invention having a generally linear fibrous stretch-resisting member.
Figure 1B:
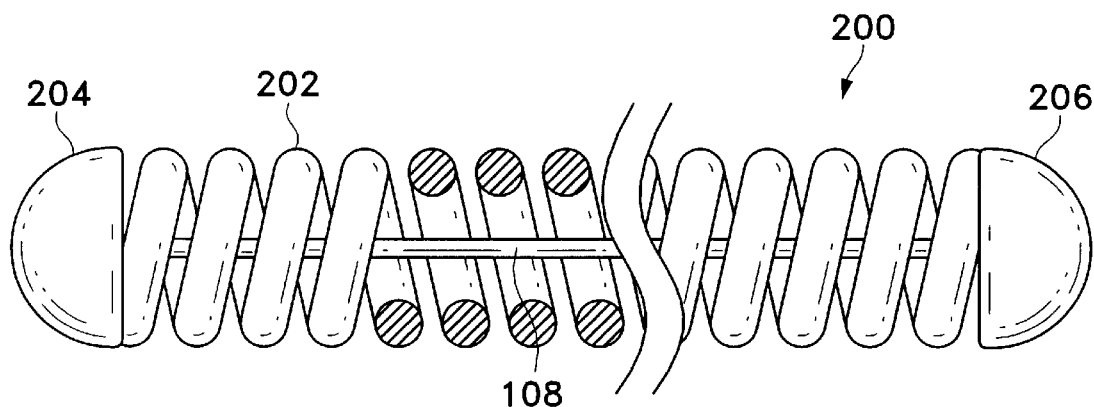
FIG. 1B shows a side view, partial cutaway of a vaso-occlusive coil made according to the invention having a generally linear wire stretch-resisting member.
Figure 1C:
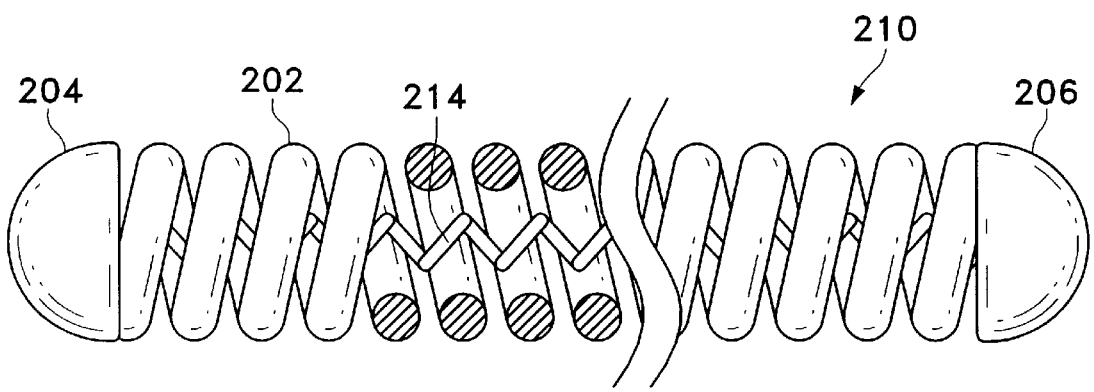
FIG. 1C shows a side view, partial cutaway of a vaso-occlusive coil made according to the invention having a generally helical stretch-resisting member.

FIGS. 1A, 1B, and 1C show side-view partial cross-sections (or cutaways) of highly desirable variations of the inventive coil (100, 200, 210).

The variations shown in FIGS. 1A and 1B are made up of a helically wound outer coil (102, 202) having a first end (104, 204) and a second end (106, 206). We refer to this form as the as the "primary" winding or shape or form. TIhese variations include a stretch-resisting member (108, 208, 214) which is shown to be fixedly attached both to the first end (104, 204) and to the second end (106, 206). In certain circumstances, it may be desirable to attach the stretchresisting member (108, 208) only to one of the two ends, to at least one site between the to ends, or to neither of the two ends. Clearly, for attaining stretch resistance, the stretch-resisting member must be attached to at least two points on the coil.

The stretch-resisting member (108) of the variation shown in FIG. 1A is fibrous and desirably polymeric. The stretch-resisting member (108) may be thermoplastic or thermosetting and comprise a bundle of threads or a single filament melted onto, glued, or otherwise fixedly attached to the vaso-occlusive coil (100).

In this variation of the invention, the stretch-resisting member is preferably a polymer (natural or synthetic) which may be heat-set in the secondary form in situ. The use of heat-treated or heat-formed polymeric filaments (monofilaments or threads) should not affect the secondary shape of the coil and provides stretch resistance while allowing the selected form of the device to perform its occlusive function without interference from the safety component. In some instances, it may also be desirable to include one or more metallic strands in the stretch-resisting member (108) to provide stiffness or electrical conductance for specific applications.

The stretch-resisting member (208) of the variation shown in FIG. 1B is a simple wire or "ribbon" which is soldered, brazed, glued, or otherwise fixedly attached to the first end (204), second end (206), or to the coil at one or more locations intermediate to those the ends.

The variation shown in FIG. 1C includes a stretch-resisting member (214) which is comprised of a helically wound coil which is soldered, brazed, glued, or otherwise fixedly attached to the first end (204) or second end (206) or in one or more intermediate locations. The stretch-resisting member (214) in this configuration provides a greater measure of lateral flexibility than the wire variation (208 in FIG. 1B). It may be wound in either the same direction as is the outer coil (202) or in the alternate direction. A modest drawback to this variation is that it will stretch more than the FIG. 1B variation when axially stressed.

The materials used in constructing the vaso-occlusive coil (102, 202) and the stretch-resisting member (108, 208, 214) may be any of a wide variety of materials; preferably, a radio-opaque material such as a metal or a polymer is used. Suitable metals and alloys for the wire making up the primary coil (102, 202) and the stretch-resisting member (108, 208, 214) include the Platinum Group metals, especially platinum, rhodium, palladium, rhenium, as well as tungsten, gold, silver, tantalum, and alloys of these metals. These metals have significant radio-opacity and in their alloys may be tailored to accomplish an appropriate blend of flexibility and stiffness. They are also largely biologically inert. Highly preferred is a platinum/tungsten alloy, e.g., 8% tungsten and the remainder platinum.

In some variations of the invention, the ribbon or coil stretch-resisting members (208, 214) may be of any of a wide variety of stainless steels if some sacrifice of radio-opacity and flexibility may be tolerated. Very desirable materials of construction, from a mechanical point of view, are materials which maintain their shape despite being subjected to high stress. Certain "super-elastic alloys" include various nickel/titanium alloys (48–58 atomic % nickel and optionally containing modest amounts of iron); copper/zinc alloys (38–42 weight % zinc); copper/zinc alloys containing 1–10 weight % of beryllium, silicon, tin, aluminum, or gallium; or nickel/aluminum alloys (36–38 atomic % aluminum). Particularly preferred are the alloys described in U.S. Pat. Nos. 3,174,851; 3,351,463; and 3,753,700. Especially preferred is the titanium/nickel alloy known as "nitinol". These are very sturdy alloys which will tolerate significant flexing without deformation even when used as very small diameter wire.

If a super-elastic alloy such as nitinol is used in the device, the diameter of the coil wire may be significantly smaller than that used when the relatively more ductile platinum or platinum/tungsten alloy is used as the material of construction.

The coils may be made of radiolucent fibers or polymers (or metallic threads coated with radiolucent or radio-opaque fibers) such as Dacron (polyester), polyglycolic acid, polylactic acid, fluoropolymers (polytetrafluoro-ethylene), Nylon (polyamide), or even cotton or silk. Should a polymer be used as the major component of the vaso-occlusive coil member, it is desirably filled with some amount of a radio-opaque material such as powdered tantalum, powdered tungsten, bismuth oxide, barium sulfate, and the like.

The coil material is first wound into a primary coil (102, 202). The primary coil is typically linear after it has been wound. Generally speaking, when the coil (102, 202) is a metallic coil and that coil is a platinum alloy or a super-elastic alloy such as nitinol, the diameter of the wire used in the production of the coil (102, 202) will be in the range of 0.00025 and 0.006 inches. The wire is wound into a primary coil (102, 202) having a primary diameter of between 0.003 and 0.025 inches. For most neurovascular indications, the preferable primary coil (102,202) diameter is 0.008 to 0.018 inches. We have generally found that the coil wire may be of sufficient diameter to provide a hoop strength to the resulting device sufficient to hold the device in place within the chosen body site, lumen or cavity, without substantially distending the wall of the site and without moving from the site as a result of the repetitive fluid pulsing found in the vascular system. However, this inventive concept allows the user to utilize extremely flexible coil assemblies having very high packing efficiencies. For instance, coil wires having wire diameters of 0.00015" and less are suitable for such highly flexible devices. Typically the coil diameter will be 0.015" and less. They will "droop" more than about 20°, preferably 35° to 90° when about 1 centimeter of the primary form of the coil having a free end is held horizontally.

The axial length of the primary coil will usually fall in the range of 0.5 to 100 cm, more usually 2.0 to 40 cm. Depending upon usage, the coil may well have 10–75 turns per centimeter, preferably 10–40 turns per centimeter. All of the dimensions here are provided only as guidelines and are not critical to the invention. However, only dimensions suitable for use in occluding sites within the human body are included in the scope of this invention.

Once the primary coil (102, 202) is wound, the stretch-resisting member (108, 208) is inserted into the lumen of the primary coil (102, 202) and secured to the coil as desired. Ends (104, 204, 106, 206) are preferably of the same diameter as is the primary coil (102, 202).

Alternatively, the primary coil is shaped into its secondary form, and heat treated so that the coil will return to the secondary form when relaxed. The stretch-resistant member is then inserted into the lumen of the coil and secured as desired. The stretch-resisting member does not substantially affect the shape of the coil when the coil returns to the secondary form. Preferably, the stretch-resistant member is attached to a hook inside the lumen and heat treatment used to fuse at least parts of the polymer to the coil. The coil is then allowed to relax to form its secondary form and any stretch-resistant filaments extending from the coil are heat sealed to the coil. It is required that there be some amount of slack in the polymer to allow the coil to pass through the catheter as described herein and to allow the coil to return to its secondary form. The secondary coil may be heated treated. Preferably, heat treatment occurs at a temperature from at least about the $T_g$ of the polymer to a temperature below the melting point of polymer.

Suitable polymeric materials for the polymeric stretch-resisting member (108) can be either thermosetting or thermoplastic. For this variation of the invention, however, the polymer should be one for which a filament may be heat-treated to accept a form corresponding to the secondary form. Thermoplastics are preferred because they allow simplification of the procedure for constructing the device (100) since they may be melted and formed into the end or ends (104, 106). Simple devices such as soldering irons may be used to form the ends. Thermosetting plastics would typically be held in place by an adhesive. Suitable polymers include most biocompatible materials which may be made into fibers but include thermoplastics, e.g., polyesters such as polyethyleneterephthalate (PET) especially Dacron; polyamides including the Nylons; polyolefins such as polyethylene, polypropylene, polybutylene, their mixtures, alloys, block and random copolymers; polyglycolic acid; polylactic acid; fluoropolymers (polytetrafluoro-ethylene), or even silk or collagen. The stretch-resistant polymer may be made from materials used as dissolvable sutures, for instance polylactic acid or polyglycolic acid, to encourage cell growth in the aneurysm after their introduction. Preferred because of the long history of safe and effective usage in the human body are fibrous PET (sold as Dacron) and polypropylene. Highly preferred is polypropylene, for instance, in the form of 10–0 and 9–0 polypropylene suture material. We have found that the diameter of the polymer is typically between about 0.0001 inches and about 0.01 inches.

FIG. 2A shows a side-view partial cross-section of one end of inventive coil (100). FIG. 2A also shows the helically wound outer coil (102) having an end (106) which is formed from a formerly molten fiber which also makes up the stretch-resisting member (114). An end of this type may be considered to have modestly higher vaso-occluding properties than a metallic end. Other functional equivalents to this structure include ends (106) formed of glues such as epoxies and their equivalents, and which are mechanical in nature.

FIG. 2B shows an external knot (112) which fixes the length of the coil member (102) and keeps it from stretching; FIG. 2C shows a reformed mass of formerly molten polymer or of glue which is of a diameter larger than the inner diameter of coil (102) and prevents the coil from stretching. The knot (112) and block (114) are not shown to be attached to the coil (102) but may be.

The variations shown in FIGS. 1A, 1B, 1C and 2A, 2B, and 2C are designed to be deployed by use of a pusher and a catheter in the manner discussed in Ritchart et al, discussed above. Other methods (and concomitant fixtures or joints to accomplish those methods) may also be used.

For instance, the end of the device may be adapted to accept an electrolytically severable joint of the type discussed in U.S. Pat. No. 5,354,295 and its parent, 5,122,136, both patents to Guglielmi and Sepetka, described above. FIGS. 3A and 3B depict, in partial cross section, such variations. The vaso-occlusive coil (130, 230) is attached to a fill member or bushing (132, 232). The fill member or bushing (132, 232) preferably comprises a thermoplastic formed into place or an epoxy or the like and adheres, in turn, both to the stretch resistant member (134, 234) and the core wire (136, 236). The stretch-resisting member (134, 234) is thusly indirectly attached to the vaso-occlusive coil (130, 230) via the fill member or bushing (132, 232). The core wire (136, 236) in this variation has an enlarged member which is embedded in the fill member (132, 232). The core wire (136, 236) is insulated, typically with a combination of polytetrafluoroethylene and PARYLENE (polyparaxyxylene), except for a small sacrificial joint (138, 238) which is intended to be the site of the electrolysis as the joint (138, 238) is eroded or severed and the coil deployed into the body site. The details of this variation (sans stretch-resistant member (136, 236)) are discussed in Gia et al, U.S. patent application Ser. No. 08/367,061, filed Dec. 30, 1994, the entirety of which is incorporated by reference.

FIG. 3C shows an especially preferred variation of the inventive device. The assembly (131) employs a stretch-resisting member (133) which is connected indirectly to the coil (135). Specifically the stretch-resisting member (133) is a thermoplastic fiber or fibers which are melted to form a coil tip (137) at one end of the coil (135) and is looped about a hook (139) at (or in the vicinity of) the other end of the coil (135). An anchor coil (141) is coaxially situated between the vaso-occlusive coil (135) and the pusher wire (136). The hook (139) forms the final turn or half-turn of the anchor coil (141). The stretch-resisting member (133) is thusly indirectly attached to the vaso-occlusive coil (135) via the anchor coil (141). The anchor coil (141) and the vaso-occlusive coil (135) are preferably welded together.

FIG. 3C also shows the vaso-occlusive coil (135) in its maximum stretched condition. The stretch-resisting member (133) is shown resisting further axial stretching of the assembly. When the vaso-occlusive coil (135) is not stretched, the stretch-resisting member (133) would obviously be loose, i.e., normally longer than the lumen, in the lumen of the assembly (131). If the stretch-resisting member (133) is not allowed to have such a loose axial fit, the adjacent turns of the coil (135) would "bottom" against each other during passage through turns in the vasculature and cause the assembly (131) to become stiff.

FIG. 4A shows still another variation of a joint for releasing the inventive coil into a site within the human body. In this instance, the joint is mechanically deployed. The primary coil (140) incorporates interlocking clasps, one (142) located on an end of the coil (140) and one (144) located on the end of a pusher (146). The stretch-resisting member (148) is attached to the interlocking clasp (142) via a filler block (154). Again, the filler block (154) comprises a material (e.g., a thermoplastic or adhesive material) which may be placed in the coil and will adhere to the stretch-resistant member (148). The coil assembly (150), made up of the primary coil (140), interlocking clasp (142), and stretch-resisting member (148) is deployed by retracting catheter body (or sheath) (152). FIG. 4B shows a variation of the device depicted in FIG. 4A which does not employ special filler block material (154) for adhering to the stretch-resistant member.

Other mechanically deployable joints suitable for use with the inventive coil are described in:

U.S. Pat. No. 5,234,437, to Sepetka, (shows a method of unscrewing a helically wound coil from a pusher having interlocking surfaces).

U.S. Pat. No. 5,250,071, to Palermo, (shows an embolic coil assembly using interlocking clasps mounted both on the pusher and on the embolic coil)

U.S. Pat. No. 5,261,916, to Engelson, (shows a detachable pusher/vaso-occlusive coil assembly having an interlocking ball and keyway-type coupling)

U.S. Pat. No. 5,304,195, to Twyford et al. (shows a pusher-vaso-occlusive coil assembly having an affixed, proximally extending wire carrying a ball on its proximal end and a pusher having a similar end, which two ends are interlocked and disengage when expelled from the distal tip of the catheter)

U.S. Pat. No. 5,312,415, to Palermo (also shows a method for discharging numerous coils from a single pusher by use of a guidewire which has a section capable of interconnecting with the interior of the helically wound coil).

U.S. Pat. No. 5,350,397, to Palermo et al. (shows a pusher having a throat at its distal end and a pusher through its axis. The pusher sheath will hold onto the end of an embolic coil and will then be released upon pushing the axially placed pusher wire against the member found on the proximal end of the vaso-occlusive coil).

The entirety of which are incorporated by reference.

As was noted above, the devices of this invention may have the simple linear shape shown in FIGS. 1 and 2 or may have shapes which are not so simple. FIGS. 5, 6, and 7 show what are termed "secondary" shapes in that they are formed from the primary coil by the simple act of winding the primary coil on a form of a desired shape and then heat treating the so-formed shape. FIG. 5 shows a "C" shaped coil assembly (160) having a stretch-resistant member (1 62). FIG. 6 shows a clover-leaf shaped coil assembly (164)

also having a stretch-resistant member (162). FIG. 7 shows a double-loop coil assembly (166). These are indicative of the various secondary shapes suitable for this invention.

Additionally, these inventive devices may also be used in conjunction with various external fiber adjuncts. FIG. 8 shows a partial side-view of a linear variation of the inventive device (170) having filamentary material (172) looping through the coil (174). This method of attachment is described in greater detail in U.S. Pat. Nos. 5,226,911 and 5,304,194, to Chee et al, the entirety of which are incorporated by reference. A further description of a desirable fiber attachment is shown in U.S. patent application No. 08/265, 188, to Mirigian et al, filed Jun. 24, 1994.

FIG. 9 shows a partial cutaway of a device (180) having a braided covering (182) of a filamentary material and a stretch-resisting member (184). This method of enveloping a coil is described in greater detail in U.S. Pat. No. 5,382, 259, to Phelps et al, the entirety of which is incorporated by reference.

The fibrous woven or braided tubular materials may be made from a biocompatible materials such as Dacron (polyester), polyglycolic acid, polylactic acid, fluoropolymers (polytetrafluoroethylene), Nylon (polyamide), or silk. The strands forming the braid should be reasonably heavy, e.g., having tensile strength of greater than about 0.15 pounds. The materials mentioned, to the extent that they are thermoplastics, may be melted or fused to the coils. Alternatively, they may be glued or otherwise fastened to the coils. Preferred materials include Dacron.

FIG. 10 shows a variation in which the stretch-resistant member is a heat-set polymer introduced into the interior lumen after the coil has been shaped to return to its secondary shape. The coil (191) is wound to a primary shape and is then shaped into a secondary form. The coil is treated, for instance by heat-treatment, so that it will maintain that secondary form. One end of the coil has an interior lumen (192) and a hook (199) within the lumen (192). The coil is then positioned so that the stretch-resistant thread (193) is introduced through the lumen (192) of the coil (191) and extended to catch the hook portion (199) in the lumen (192) of the coil (191). The end of the coil with the hook is then heated so that several turns of the exterior coil contact and are melted to the stretch-resistant polymer (193). The coil (191) is then allowed to form its secondary shape. Any filaments of stretch-resistant polymer which extend from the coil (191) are heat-sealed (197). Some amount of slack in the filament is required. The stretch-resistant polymer through the lumen must be flexible enough so that they do not change the secondary shape of the coil. The entire coil (191) is then heat-treated at a temperature below the melting point of the polymer. Preferably, the temperature is above the polymer's $T_g$ range.

FIG. 11 shows a highly preferred assembly incorporating a number of desirable aspects of the invention. Specifically, the very flexible variation of the inventive vaso-occlusive device noted above, e.g., wherein the vaso-occlusive device is capable of "drooping" 20° or more and having a polymeric stretch-resistant member included therein, is especially suitable for inclusion in a flow-directed catheter and particularly when used with an electrolytically severable joint. FIG. 10 shows the flow-directed catheter (200) containing a very flexible vaso-occlusive coil (202) as described above and utilizing a similarly flexible strain-resistant member (204). The flow directed catheter (200) may have a distal radioopaque marker (206) if so desired.

Proximally of the vaso-occlusive coil (202) is a connective wire (208) which is insulated at all points proximal of the electrolytic joint (210).

The flow directed catheter (200) may be of any known design such as is found, e.g., in U.S. Pat. No. 5,336,205, to Zenzen et al, the entirety of which is incorporated by reference. "Flow-directed catheters" are directed to the treatment site in the human body through the vasculature by the motive power of natural blood flow. The more distal segments of flow-directed catheters are often of materials having significant elastomeric properties but with high burst strengths, e.g., polyurethane, polyvinylchloride, silicones, etc. They are often quite "rubbery" in feel. Consequently, flow directed catheters are not usually especially suitable for use with guidewires and the like.

In use of this variation of the vaso-occlusive device, however, since the vaso-occlusive device is so compliant and able to be delivered using hydraulic pressure alone (as with saline), they may be used with flow-directed catheters. Further, since the vaso-occlusive device (202) contains a stretch-resisting member (204), the vaso-occlusive device (202) may be withdrawn into the catheter (200) using the connective wire (208).

The connective wire (208) used therein should be very flexible so not to interfere with the movement of the catheter (200). It is conductive and insulated proximally of the electrolytic joint (210). Introduction of an electric current into the connective wire (208) will cause the electrolytic joint (210) to erode and the vaso-occlusive device (202) to become detached. Complete description of the operation of such a device is found in U.S. Pat. Nos. 5,122,136 and 5,354,295, both to Guglielmi and Sepetka.

Figure 12A:
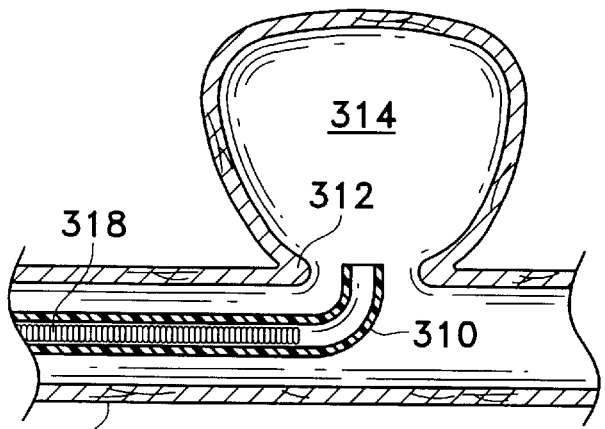
Figure 12B:
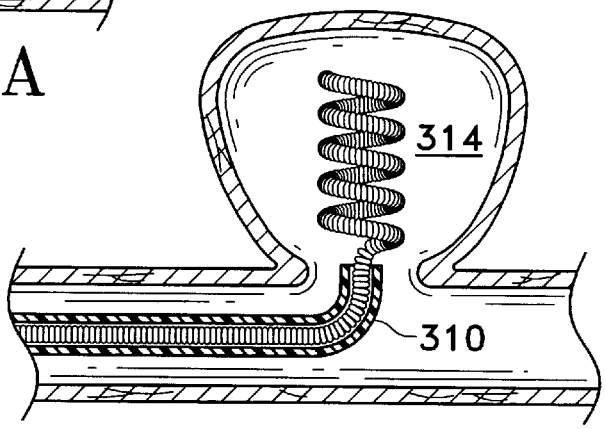
Figure 12C:
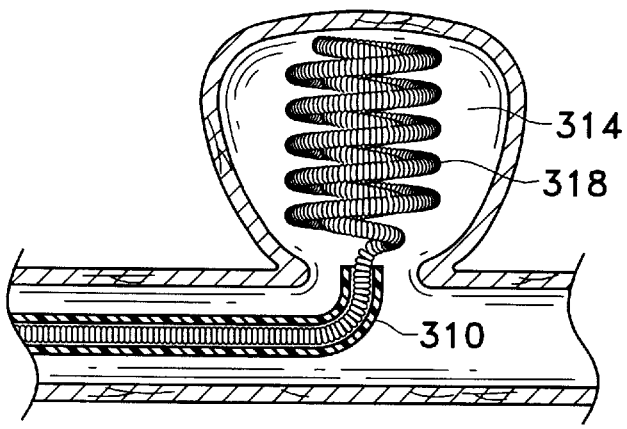
Figure 12D:
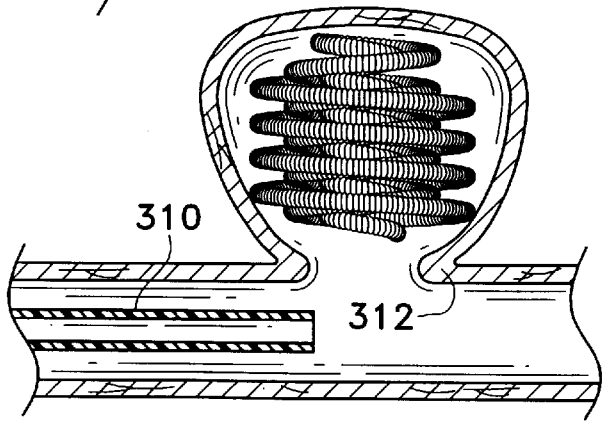

FIGS. 12A–12D depict a common deployment method for introduction of the inventive vaso-occlusive devices described here. It may be observed that these procedures are not significantly different than those described in the Ritchart et al. patent mentioned above. Specifically, FIG. 12A shows the distal tip of a delivery catheter (310) which is within the opening (312) of an aneurysm (314) found in an artery (316). The distal or end section of the vaso-occlusive device (318) is shown within the catheter (310). In FIG. 12B, the distal end portion of the vaso-occlusive device (318) has exited the distal end of the catheter (310) and has wound into a secondary shape within the aneurysm (314). FIG. 12C shows the completion of the formation of the secondary shape within the aneurysm (314). FIG. 12D shows the separation of the vaso-occlusive device (318) from the pusher, placement within the aneurysm (314), and the withdrawal of the catheter from the mouth of the aneurysm.

Once the inventive coil is in place in an aneurysm or other site, there may be an occasion during which the coil must be moved or even withdrawn. For instance, in FIG. 12D, the coil might extend through the mouth (312) of the aneurysm into the artery. Occlusion would not be desirable in the artery. A device such as the endovascular snare shown in U.S. Pat. No. 5,387,219, to Rappe, may then be used to grasp the exposed coil and move it or retrieve it from the body. The stretch-resisting member of this invention prevents the coil from stretching into a single strand of wire and multiplying in length.

Modification of the above-described variations of carrying out the invention that would be apparent to those of skill in the fields of medical device design generally, and vaso-occlusive devices specifically, are intended to be within the scope of the following claims.

We claim as our invention:

1. A vaso-occlusive device comprising:
   i. an outer helically wound coil having a primary shape, first end, and a second end, said coil defining a lumen between said first end and second end, the helically wound coil further having a secondary shape different from the primary shape; and ii. a stretch-resisting member comprising at least one polymeric filament having a first end and a second end, the stretch-resisting member extending through at least a portion of said lumen, said stretch-resisting member not substantially affecting the shape of said coil when said coil is in said secondary shape, and said stretch-resisting member being attached to said coil in at least two locations.

2. The device of claim 1 wherein the stretch-resisting member has been heat-treated in said lumen when said coil is in said secondary.

3. The device of claim 1 wherein the polymeric filament is thermoplastic.

4. The device of claim 1 wherein the polymeric filament is melted onto at least several helical turns of the coil.

5. The device of claim 1 wherein the first end of the polymeric filament is sealed to the first end of the coil to form a cap and the second end of the polymeric filament is sealed to the second end of the coil to form a cap.

6. The device of claim 1 wherein the stretch-resisting member has been secured to said coil when the coil is in the secondary shape.

7. The device of claim 1 comprising a deployment tip attached to at least one of said first end or said second end of said coil.

8. The device of claim 7 wherein said deployment tip comprises a mechanically detachable end adapted to attach to and detach from a pusher.

9. The device of claim 7 wherein said deployment tip comprises an electrolytically detachable end adapted to detach from a pusher by imposition of a current on said pusher.

10. The device of claim 1 wherein said helically wound coil comprises a metal selected from the group consisting of platinum, palladium, rhodium, gold, tungsten, and their alloys.

11. The device of claim 10 wherein said helically wound coil comprises an alloy of platinum and tungsten.

12. The device of claim 1 wherein said helically wound coil comprises an alloy selected from the group consisting of stainless steels and superelastic alloys.

13. The device of claim 12 wherein said helically wound coil comprises a nickel-titanium super-elastic alloy.

14. The device of claim 1 comprising a polymer containing a radio-opaque filler.

15. The device of claim 1 additionally comprising external filamentary material attached to said primary coil.

16. The device of claim 1 wherein the stretch-resisting member comprises a polymeric filament selected from the group consisting of polypropylene, polyethylene terephthalate, nylon, polyethylene, polybutylene, polyglycolic acid, polylactic acid, polytetrafluoroethylene, silk, and collagen.

17. The device of claim 16 wherein said stretch-resisting member comprises polypropylene.

18. The device of claim 17 wherein the stretch-resisting member comprises 10-0 polypropylene sutures.

19. The device of claim 17 wherein the stretch-resisting member comprises 9-0 polypropylene sutures.

20. The device of claim 1 wherein said cap is of the same diameter as said primary coil.

21. The device of claim 1 wherein the helically wound primary coil has a flexibility such that one free centimeter will flex more than about 20° when held horizontally.

22. The device of claim 1 further comprising, in combination, a flow-directed catheter surrounding at least a portion of said helically wound primary coil.

23. A vaso-occlusive device comprising:

i. an outer helically wound coil having a primary shape, first end, and a second end, said coil defining a lumen between said first end and second end, the helically wound coil further having a secondary shape different from the primary shape; and ii. a stretch-resisting member comprising at least one polymeric filament having a first end and a second end, the stretch-resisting member extending through at least a portion of said lumen, said stretch-resisting member not substantially affecting the shape of said coil when said coil is in said secondary shape, said stretch-resisting member being attached to said coil in at least two locations, and said stretch-resisting member being fixedly attached to a hook within the lumen of said coil.

24. The device of claim 23 wherein the stretch-resisting member has been heat-treated in said lumen when said coil is in said secondary shape.

25. The device of claim 23 wherein the polymeric filament is thermoplastic.

26. The device of claim 23 wherein the polymeric filament is melted onto at least several helical turns of the coil.

27. The device of claim 23 wherein the first end of the polymeric filament is sealed to the first end of the coil to form a cap and the second end of the polymeric filament is sealed to the second end of the coil to form a cap.

28. The device of claim 23 wherein the stretch-resisting member has been secured to said coil when the coil is in the secondary shape.

29. The device of claim 23 comprising a deployment tip attached to at least one of said first end or said second end of said coil.

30. The device of claim 29 wherein said deployment tip comprises a mechanically detachable end adapted to attach to and detach from a pusher.

31. The device of claim 29 wherein said deployment tip comprises an electrolytically detachable end adapted to detach from a pusher by imposition of a current on said pusher.

32. The device of claim 23 wherein said helically wound coil comprises a metal selected from the group consisting of platinum, palladium, rhodium, gold, tungsten, and their alloys.

33. The device of claim 32 wherein said helically wound coil comprises an alloy of platinum and tungsten.

34. The device of claim 23 wherein said helically wound coil comprises an alloy selected from the group consisting of stainless steels and super-elastic alloys.

35. The device of claim 34 wherein said helically wound coil comprises a nickel-titanium super-elastic alloy.

36. The device of claim 23 comprising a polymer containing a radio-opaque filler.

37. The device of claim 23 additionally comprising external filamentary material attached to said primary coil.

38. The device of claim 23 wherein the stretch-resisting member comprises a polymeric filament selected from the group consisting of polypropylene, polyethylene terephthalate, nylon, polyethylene, polybutylene, polyglycolic acid, polylactic acid, polytetrafluoroethylene, silk, and collagen.

39. The device of claim 38 wherein said stretch-resisting member comprises polypropylene.

40. The device of claim 39 wherein the stretch-resisting member comprises 10-0 polypropylene sutures.

41. The device of claim 40 wherein the stretch-resisting member comprises 9-0 polypropylene sutures.

42. The device of claim 23 wherein said cap is of the same diameter as said primary coil.

43. The device of claim 23 wherein the helically wound primary coil has a flexibility such that one free centimeter will flex more than about 20° when held horizontally.

44. The device of claim 23 further comprising, in combination, a flow-directed catheter surrounding at least a portion of said helically wound primary coil.

* * * * *